United States Patent
Inoue et al.

(10) Patent No.: US 11,913,061 B2
(45) Date of Patent: Feb. 27, 2024

(54) METHOD FOR PREPARING NUCLEIC ACID SAMPLE

(71) Applicant: KAO CORPORATION, Tokyo (JP)

(72) Inventors: Takayoshi Inoue, Utsunomiya (JP); Akira Hachiya, Utsunomiya (JP)

(73) Assignee: KAO Corporation, Tokyo (JP)

( * ) Notice: Subject to any disclaimer, the term of this patent is extended or adjusted under 35 U.S.C. 154(b) by 190 days.

(21) Appl. No.: 15/781,644

(22) PCT Filed: Jun. 7, 2017

(86) PCT No.: PCT/JP2017/021040
§ 371 (c)(1),
(2) Date: Jun. 5, 2018

(87) PCT Pub. No.: WO2018/008319
PCT Pub. Date: Jan. 11, 2018

(65) Prior Publication Data
US 2018/0371524 A1    Dec. 27, 2018

(30) Foreign Application Priority Data

Jul. 8, 2016 (WO) .................. PCT/JP2016/070343

(51) Int. Cl.
| | | |
|---|---|---|
| C12Q 1/68 | (2018.01) | |
| C07H 21/04 | (2006.01) | |
| C12Q 1/6806 | (2018.01) | |
| C12N 15/09 | (2006.01) | |
| B32B 5/18 | (2006.01) | |
| C12Q 1/6886 | (2018.01) | |
| C12Q 1/6883 | (2018.01) | |
| C12Q 1/686 | (2018.01) | |

(52) U.S. Cl.
CPC .............. *C12Q 1/6806* (2013.01); *B32B 5/18* (2013.01); *C12N 15/09* (2013.01); *C12Q 1/68* (2013.01); *C12Q 1/686* (2013.01); *C12Q 1/6883* (2013.01); *C12Q 1/6886* (2013.01); *C12Q 2600/112* (2013.01); *C12Q 2600/118* (2013.01); *C12Q 2600/158* (2013.01); *C12Q 2600/16* (2013.01); *C12Q 2600/166* (2013.01); *C12Q 2600/178* (2013.01)

(58) Field of Classification Search
None
See application file for complete search history.

(56) References Cited

U.S. PATENT DOCUMENTS

| | | | | |
|---|---|---|---|---|
| 6,649,181 | B1 * | 11/2003 | Miner ..................... | A61Q 19/00 424/443 |
| 2002/0110655 | A1 * | 8/2002 | Seth ......................... | B32B 5/18 428/35.2 |
| 2002/0155234 | A1 * | 10/2002 | Seth ......................... | A47K 7/00 428/35.2 |
| 2005/0221334 | A1 | 10/2005 | Benson | |
| 2005/0260176 | A1 | 11/2005 | Ayares et al. | |
| 2008/0226580 | A1 | 9/2008 | Maeda et al. | |
| 2010/0285463 | A1 | 11/2010 | Kronenberg et al. | |
| 2013/0259924 | A1 | 10/2013 | Bancel et al. | |
| 2014/0256584 | A1 | 9/2014 | Chang | |
| 2014/0274789 | A1 | 9/2014 | Keller et al. | |
| 2014/0287942 | A1 | 9/2014 | Mahmood et al. | |
| 2015/0086581 | A1 | 3/2015 | Li et al. | |
| 2015/0133311 | A1 | 5/2015 | Uchiyama | |
| 2015/0285787 | A1 | 10/2015 | Msika et al. | |
| 2015/0301058 | A1 | 10/2015 | Schettini et al. | |

FOREIGN PATENT DOCUMENTS

| | | |
|---|---|---|
| CN | 103782174 A | 5/2014 |
| EP | 1 980 235 A1 | 10/2008 |
| JP | 2005-192409 A | 7/2005 |
| JP | 2010-115178 A | 5/2010 |
| JP | 2011-19505 A | 2/2011 |
| JP | 2011-520451 A | 7/2011 |
| JP | 2015-512255 A | 4/2015 |
| JP | 2015-518705 A | 7/2015 |
| JP | 2015-528699 A | 10/2015 |
| JP | 2016-011283 A | 1/2016 |
| JP | 2016-509471 A | 3/2016 |
| JP | 2016-103997 A | 6/2016 |
| JP | 2016-105861 A | 6/2016 |
| KR | 10-2008-0031590 A | 4/2008 |
| WO | WO 00/09754 A2 | 2/2000 |
| WO | WO 2012/109157 A2 | 8/2012 |
| WO | WO 2012/109157 A3 | 8/2012 |
| WO | WO 2012/170711 A1 | 12/2012 |
| WO | WO 2013/142378 A1 | 9/2013 |
| WO | WO 2013/151666 A2 | 10/2013 |
| WO | WO-2013/179672 A1 | 12/2013 |
| WO | WO 2014/082083 A1 | 5/2014 |
| WO | WO 2014/093934 A1 | 6/2014 |
| WO | WO 2016/172598 A1 | 10/2016 |
| WO | WO 2016/191644 A1 | 12/2016 |

OTHER PUBLICATIONS

Downing (The Journal of Investigative Dermatology 79:226-228, 1982).*
Benson et al. An Analysis of Select Pathogenic Messages in Lesional and Non-Lesional Psoriatic Skin Using Non-Invasive Tape Harvesting. Journal of Investigative Dermatology;2006;126:2234-2241. (Year: 2006).*
Pressure Biosciences Inc. (BPI), Detection of Propionibacterium acnes 16S rRNA and Lipase Genes from Sebum Samples Collected on Lipid-specific Adhesive Skin Strips and Processed by Pressure Cycling Technology (PCT) , https://www.pressurebiosciences.com/news/publications-by-type. (Year: 2009).*
Berge et al. A collaborative European exercise on mRNA-based body fluid/skin typing and interpretation of DNA and RNA results. Forensic Science International: Genetics;2014;10: 40-48. (Year: 2014).*

(Continued)

*Primary Examiner* — Jeanine A Goldberg
(74) *Attorney, Agent, or Firm* — Foley & Lardner LLP

(57) ABSTRACT

Provided is a method by which a nucleic acid sample can be collected from a subject minimally invasively. A method for preparing a nucleic acid derived from a skin cell of a subject, comprising isolating the nucleic acid from skin surface lipids collected from the subject.

9 Claims, 4 Drawing Sheets
Specification includes a Sequence Listing.

(56) References Cited

OTHER PUBLICATIONS

Perry and Lamber. Propionibacterium. Letters in Applied Microbiology 42 (2006) 185-188. (Year: 2006).*
Luca and Valacchi. Surface Lipids as Multifunctional Mediators of Skin Responses to Environmental Stimuli. Mediators of Inflammation;2010; vol.; 2010, Article ID 321494, 11 pages. (Year: 2010).*
Smith and Thiboutot. Sebaceous gland lipids: friend or foe? Journal of Lipid Research;2008;49:271-281. (Year: 2008).*
Benson et al. An Analysis of Select Pathogenic Messages in Lesional and Non-Lesional Psoriatic Skin Using Non-Invasive Tape Harvesting. Journal of Investigative Dermatology;2006;126:2234-2241. (Year: 2006) (Year: 2006).*
Pressure Biosciences Inc. (BPI), Detection of Propionibacterium acnes 16S rRNA and Lipase Genes from Sebum Samples Collected on Lipid-specific Adhesive Skin Strips and Processed by Pressure Cycling Technology (PCT) , https://www.pressurebiosciences.com/news/publications-by-type. 2 pages (2009) (Year: 2009).*
Luca and Valacchi. Surface Lipids as Multifunctional Mediators of Skin Responses to Environmental Stimuli. Mediators of Inflammation; 2010; 321494: p. 1-11. (Year: 2010).*
Ayres, Methods for Evaluating Sebum Removal, in Cosmetic Claims Substantiation; 1997; 1st Edition; ebook ISBN 9780429156984 ; p. 115-130. (Year: 1997).*
Clarys and Barel. Quantitative Evaluation of Skin Surf ace Lipids. Clinics in Dermatology; 1995; 13: 307-321. (Year: 1995).*
Lindenbergh et al. A multiplex (m)RNA-profiling system for the forensic identification of body fluids and contact traces. Forensic Science International: Genetics; 2012; 6: 565-577. (Year: 2012).*
Pressure Biosciences Inc. (PBI) Application Note, Detection of Propionibacterium acnes 16S rRNA and Lipase Genes from Sebum Samples Collected on Lipid-specific Adhesive Skin Strips and Processed by Pressure Cycling Technology (PCT)—Oct. 4, 2009; 2009; p. 1-2 . (Year: 2009).*
Alexeyev and Jahns, Anaerobe; 2012; 18: p. 479-483. (Year: 2012).*
Lindenbergh et al. Forensic Science International: Genetics; 2012; 6: 565-577. (Year: 2012).*
Ayres, James. Methods for Evaluating Sebum Removal, in Cosmetic Claims Substantiation; 1997; 1st Edition; ebook ISBN 9780429156984; p. 115-130. (Year: 1997).*
Robosky et al. (J. of Lipid Research, vol. 49, No. 3, p. 686-692, Mar. 2008) (Year: 2008).*
Search Report dated Sep. 10, 2018 for European Patent Application No. 17823926.5, 4 pages.
Haas, C., et al., "RNA/DNA co-analysis from human skin and contact traces—results of a sixth collaborative EDNAP exercise", Forensic Science International: Genetics, vol. 16, 2015, pp. 139-147.
Van Den Berge, M., et al., "Prevalence of human cell material: DNA and RNA profiling of public and private objects and after activity scenarios", Forensic Science International: Genetics, vol. 21, 2016, pp. 81-89.
Silvia Zoppis, et al., "DNA Fingerprinting Secondary Transfer from Different Skin Areas: Morphological and Genetic Studies" Forensic Science International: Genetics, vol. 11, 2014, pp. 137-143.
Titia Sijen, "Molecular Approaches for Forensic Cell Type Identification: On mRNA, miRNA, DNA Methylation and Microbial Markers" Forensic Science International: Genetics, vol. 18, 2015, pp. 21-32
International Search Report dated Jul. 11, 2017 in PCT/JP2017/021040 filed Jun. 7, 2017.
Written Opinion dated Jul. 11, 2017 in PCT/JP2017/021040 filed Jun. 7, 2017 (with English language translation).
Bernhard Ralla, et al., "Nucleic acid-based biomarkers in body fluids of patients with urologic malignancies," Critical Reviews in Clinical Laboratory Sciences, vol. 51, No. 4, 2014, pp. 200-231.
Nicholas R. Benson, et al., "An Analysis of Select Pathogenic Messages in Lesional and Non-Lesional Psoriatic Skin Using Non-Invasive Tape Harvesting," Journal of Investigative Dermatology, vol. 126, 2006, pp. 2234-2241.
Alexander Lindenbergh, et al., "A multiplex (m)RNA-profiling system for the forensic identification of body fluids and contact traces," Forensic Science International Genetics, vol. 6, 2012, pp. 565-577.
Hikaru Watanabe, et al., "Hito Hifu Saikinso Kaiseki ni yoru Kojin Tokutei," Annual Meeting of the Japanese Biochemical Society, vol. 88, 2015, 3 Pages.
Hang Fai Kwok, et al., "DNA in Amphibian and Reptile Venom Permits Access to Genomes Without Specimen Sacrifice," Genomics Insights, vol. 1, 2008, pp. 17-24.
Naoko Kito et al., "Gaibunpisen Tokuitekina microRNA no Profiling," Annual Meeting of the Molecular Biology Society of Japan Program Yoshishu, 2014, 3 Pages.
Aurélie Renvoise, et al., "*Helcobacillus massiliensis* gen. nov., sp. nov., a novel representative of the family *Dermabacteraceae* isolated from a patient with a cutaneous discharge," International Journal of Systematic and Evolutionary Microbiology, vol. 59, 2009, pp. 2346-2351.
A. Tkachenko, et al., "An assay to screen bacterial adhesion to mucus biomolecules," Letters in Applied Microbiology, vol. 56, 2012, pp. 79-82.
Laura S. Robertson, et al., "Expression analysis and identification of antimicrobial peptide transcripts from six North American frog species," Diseases of Aquatic Organisms, vol. 104, Jun. 2013, pp. 225-236.
Wentao Guo, et al., "Skin Secretion and Shedding Is a Good Source for Non-Destructive Genetic Sampling in the Chinese Giant Salamander (*Andrias davidianus*)," Verlag der Zeitschrift für Naturforschung, 2013, pp. 164-168.
Asada, Yasuo, "Sebum decomposition and indigenous skin flora," Skin, Aug. 1967, 9(3):314-320, with English machine translation.
Hair Care: Scalp and fungus, Kao, https://www.kao.com/jp/haircare/health-of-scalp/21-4/, retrieved on Oct. 29, 2021, with English machine translation.
Machida et al., "MicroRNAs in Salivary Exosome as Potential Biomarkers of Aging," Int. J. Mol. Sci., 2015, 16:21294-21309; doi: 10.3390/ijms160921294.
Martinez-Fernandez et al., "RNA Detection in Urine: From RNA Extraction to Good Normalizer Molecules," The Journal of Molecular Diagnostics, 2016, 18(1):15-22.
Ohno et al., "Development of Nucleic Acid DDS by Exosome," Drug Delivery System, 29-2, 2014 pp. 134-139, with English machine translation.

* cited by examiner

|  | No.1 | | No.2 | | No.3 | | |
|---|---|---|---|---|---|---|---|
| KRT1 | 11 | 5 | 654 | 632 | 48 | 117 | Epidermis |
| KRT10 | 123 | 64 | 12406 | 10273 | 1608 | 752 | |
| FLG | 305 | 412 | 19539 | 14853 | 1307 | 744 | |
| IVL | 156 | 241 | 22111 | 34504 | 1361 | 1484 | |
| KRT7 | 8 | 12 | 0 | 0 | 101 | 82 | Sweat gland |
| KRT8 | 38 | 63 | 102 | 33 | 72 | 56 | |
| KRT14 | 792 | 625 | 12269 | 8612 | 3887 | 3296 | |
| KRT15 | 65 | 33 | 166 | 1363 | 128 | 176 | |
| KRT18 | 4 | 14 | 311 | 98 | 15 | 22 | |
| KRT19 | 12 | 0 | 0 | 141 | 145 | 125 | |
| KRT17 | 3573 | 3587 | 132437 | 112625 | 14693 | 15910 | Hair follicle |
| KRT75 | 23 | 16 | 762 | 166 | 74 | 89 | |
| KRT79 | 262 | 213 | 14203 | 14838 | 1791 | 784 | |
| KRT16 | 1044 | 467 | 17549 | 10389 | 4022 | 3169 | |
| COL1A1 | 32 | 20 | 0 | 0 | 54 | 30 | Dermis |
| ELN | 0 | 0 | 0 | 0 | 0 | 0 | |
| COL3A1 | 0 | 0 | 0 | 0 | 0 | 0 | |
| FBN1 | 38 | 20 | 9 | 1 | 0 | 3 | |
| ACSL1 | 28221 | 27112 | 6525 | 2666 | 12416 | 11829 | Sebaceous gland |
| PPARD | 1492 | 2070 | 3406 | 4886 | 2077 | 2409 | |
| PLIN2 | 2729 | 3047 | 9543 | 8372 | 5518 | 4950 | |
| ELOVL5 | 5099 | 6610 | 2538 | 2412 | 4414 | 4490 | |
| FASN | 58 | 78 | 1396 | 544 | 268 | 251 | |

SEQUENCE LISTING

<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: Oligonucleotide primer 27F

<400> SEQUENCE: 1
agagtttgat cmtggctcag    20

<210> SEQ ID NO 2
<211> LENGTH: 18
<212> TYPE: DNA
<213> ORGANISM: Artificial
<220> FEATURE:
<223> OTHER INFORMATION: Oligonucleotide primer 519R

<400> SEQUENCE: 2
gwattaccgc ggckgctg    18

<210> SEQ ID NO 3
<211> LENGTH: 23
<212> TYPE: DNA
<213> ORGANISM: Artificial
<220> FEATURE:
<223> OTHER INFORMATION: Oligonucleotide primer NL-1

<400> SEQUENCE: 3
gcatatcaat aagcggagga aag    23

<210> SEQ ID NO 4
<211> LENGTH: 19
<212> TYPE: DNA
<213> ORGANISM: Artificial
<220> FEATURE:
<223> OTHER INFORMATION: Oligonucleotide primer NL-4

<400> SEQUENCE: 4
ggtccgtgtt tcaagacgg    19

<210> SEQ ID NO 5
<211> LENGTH: 21
<212> TYPE: DNA
<213> ORGANISM: Artificial
<220> FEATURE:
<223> OTHER INFORMATION: Oligonucleotide primer GAPDH-F

<400> SEQUENCE: 5
cccttcattg acctcaacta c    21

<210> SEQ ID NO 6
<211> LENGTH: 20
<212> TYPE: DNA
<213> ORGANISM: Artificial
<220> FEATURE:
<223> OTHER INFORMATION: Oligonucleotide primer GAPDH-R

<400> SEQUENCE: 6
agtgagcttc ccgttcagct    20

<210> SEQ ID NO 7
<211> LENGTH: 21
<212> TYPE: DNA
<213> ORGANISM: Artificial

```
<220> FEATURE:
<223> OTHER INFORMATION: Oligonucleotide primer SOD2-F

<400> SEQUENCE: 7
cccttcattg acctcaacta c                                              21

<210> SEQ ID NO 8
<211> LENGTH: 20
<212> TYPE: DNA
<213> ORGANISM: Artificial
<220> FEATURE:
<223> OTHER INFORMATION: Oligonucleotide primer SOD2-R

<400> SEQUENCE: 8
agtgagcttc ccgttcagct                                                20
```

METHOD FOR PREPARING NUCLEIC ACID SAMPLE

FIELD OF THE INVENTION

The present invention relates to a method for preparing a nucleic acid sample.

BACKGROUND OF THE INVENTION

In recent years, with the rapid development of analytical techniques, it has become possible to analyze molecules (nucleic acids, proteins, metabolites, etc.) in various biological samples in detail. Furthermore, by virtue of these molecular analyses, techniques for investigating the current and even future human in vivo physiological conditions have been under development. Among them, the analyses using nucleic acid molecules, for which comprehensive analytical methods have been established, are advantageous in that abundant information can be obtained by a single analysis and in that functional linkage of analytical results can be easily performed based on many research reports on single nucleotide polymorphisms, RNA functions, etc.

Techniques for diagnosis and prediction of diseases and the like using nucleic acid molecules in biological samples which have been collected minimally invasively or noninvasively are under development by many research institutions around the world and their application has advanced dramatically. Among them, diagnostic techniques using DNA or RNA are widely used. Diagnostic techniques using DNA are generally methods of collecting saliva or cells in the oral cavity of a subject and analyzing single nucleotide polymorphisms in the genomic DNA comprised therein to diagnose the future disease risk and the diathesis of the subject. On the other hand, diagnostic techniques using RNA are methods of diagnosing the presence or absence of current in vivo diseases based on expression data of RNA comprised in a biological sample such as blood and urine (Non Patent Literature 1).

Among various body tissues, the skin has drawn attention as a tissue from which biological sample can be collected minimally invasively, because it is in contact with the ambient environment. Conventionally, as a method for collecting a nucleic acid from the skin noninvasively or minimally invasively, peeling of the horny layer with a tape and use of the evulsed hair has been reported (Non Patent Literature 2, Patent Literature 1). However, collecting of the nucleic acid by peeling of the horny layer is disadvantageous in that dedicated tapes are required, the amount collected is a trace, only the expression data derived from the epidermis can be obtained from the collected nucleic acid, and the like. Also, the collection of nucleic acid from the evulsed hair is disadvantageous in that evulsion of the hair is accompanied by pain, only the expression data derived from the hair follicle can be obtained from the collected nucleic acid, and the like. RNA profiling has also been reported with use of a human skin sample collected by wiping the skin surface with a moistened cotton swab (cotton ball) as a method for collecting a nucleic acid from the skin noninvasively (Non Patent Literature 3). The human skin sample collected in this report is judged not to comprise lipids present on the skin surface in view of the used collection method.
(Patent Literature 1) JP-A-2005-192409
(Non Patent Literature 1) Crit Rev Clin Lab Sci, 2014, 51, 200-231
(Non Patent Literature 2) J Invest Dermatol, 2006, 126, 2234-2241
(Non Patent Literature 3) Forensic Sci Int Genet, 2012, 6(5): 565-577

SUMMARY OF THE INVENTION

In one aspect, the present invention provides a method for preparing a nucleic acid derived from a skin cell of a subject, comprising isolating the nucleic acid from skin surface lipids collected from the subject.

In another aspect, the present invention provides a method for analyzing a nucleic acid, comprising analyzing the nucleic acid prepared by the above method.

In a further aspect, the present invention provides a kit for preparing a nucleic acid derived from a skin cell of a subject, comprising a collecting tool for skin surface lipids from the subject.

BRIEF DESCRIPTION OF THE DRAWINGS

FIG. 3 Expression levels of marker genes of the epidermis, sweat gland, hair follicle, dermis and sebaceous gland in SSLs.

DETAILED DESCRIPTION OF THE INVENTION

Figure 1:
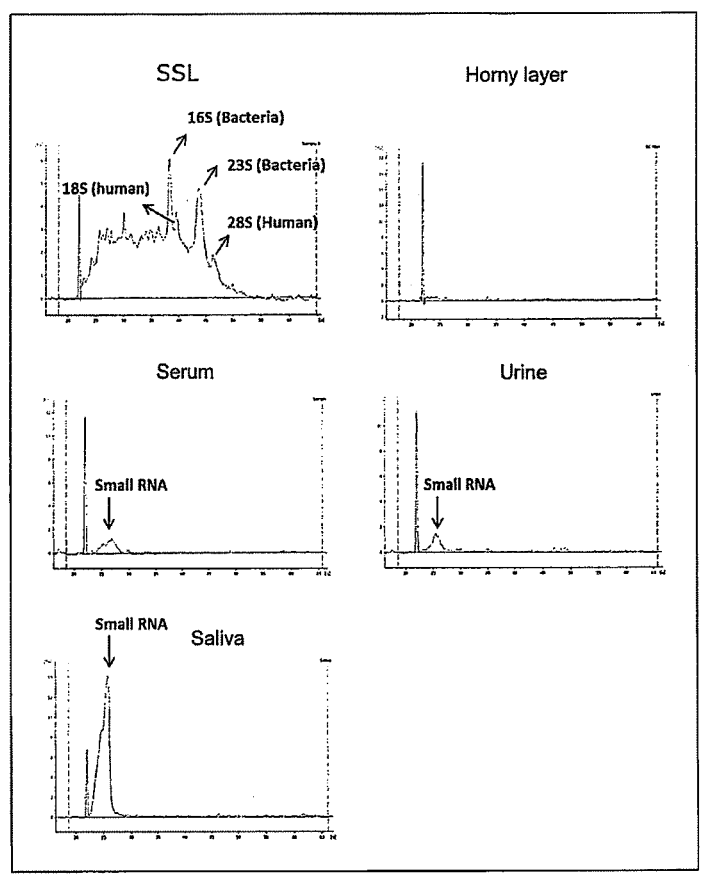
FIG. 1 RNAs comprised in various biological samples.

It is desirable to develop a method by which nucleic acid samples can be collected from a subject minimally invasively anywhere by any collector. In addition, it is further desirable to obtain nucleic acid samples from which information from the skin and other various tissues and organs can be obtained.

The present inventors found that lipids present on the skin surface of a subject comprise a nucleic acid derived from a skin cell of the subject, and that the nucleic acid reflects gene expression profiles not only in the epidermis but also in other tissues such as the sebaceous gland and hair follicle. Accordingly, the present inventors found that a gene analysis and condition diagnosis of a subject can be performed in a convenient and minimal invasive manner and more comprehensively by analyzing a nucleic acid in lipids present on the skin surface of a subject.

The present invention provides a method for preparing a nucleic acid of a subject in a convenient and minimal invasive manner, and a tool therefor. According to the present invention, a nucleic acid sample can be collected from a subject in a convenient and minimal invasive manner. The nucleic acid prepared by the present invention is useful as a sample for an analysis of gene expression and an analysis of other genetic information on the skin of a subject, a functional analysis on the skin of a subject, an analysis of skin conditions (such as a diagnosis of skin cancer) of a subject, as well as an analysis of conditions of regions other than the skin or the general condition (such as, diagnoses of various diseases) of a subject, and the like.
(Method for Preparing Nucleic Acid)

In one aspect, the present invention provides a method for preparing a nucleic acid derived from a skin cell of a subject. In one embodiment, the method for preparing a nucleic acid derived from a skin cell of a subject according to the present invention comprises isolating the nucleic acid from skin surface lipids collected from the subject.

The term "skin surface lipids; SSLs" used herein refers to a lipid-soluble fraction present on the surface of the skin, and is sometimes also referred to as sebum. Generally, SSLs mainly comprise secretions secreted from the exocrine gland such as the sebaceous gland on the skin surface and are present on the surface in the form of a thin layer covering the skin surface.

The term "skin" used herein is a generic term for regions including tissues on the body surface such as the epidermis, the dermis, the hair follicle, and the sweat gland, the sebaceous glands and other glands, unless otherwise specified.

The subject in the method of the present invention may be any organism having SSLs on the skin. Examples of the subject include mammals including a human and a non-human mammal with a human preferred. The subject is preferably a human or a non-human mammal in need of or desiring an analysis of his/her or its own nucleic acid. Alternatively, the subject is preferably a human or a non-human mammal in need of or desiring an analysis of gene expression on the skin, or an analysis of conditions of the skin or regions other than the skin using a nucleic acid.

The SSLs collected from the subject comprise nucleic acids expressed in a skin cell of the subject, preferably nucleic acids expressed in any of the epidermis, sebaceous gland, hair follicle, sweat gland and dermis, and more preferably nucleic acids expressed in any of the epidermis, sebaceous gland, hair follicle and sweat gland. Therefore, the nucleic acid derived from a skin cell of a subject and prepared by the method of the present invention is preferably a nucleic acid derived from at least one region selected from the group consisting of the epidermis, sebaceous gland, hair follicle, sweat gland and dermis of the subject, and more preferably a nucleic acid derived from at least one region selected from the group consisting of the epidermis, sebaceous gland, hair follicle and sweat gland.

Examples of the nucleic acid derived from a skin cell of a subject and prepared by the method of the present invention include, but not particularly limited to, DNA and RNA, and is preferably RNA. Examples of RNA include mRNA, tRNA, rRNA, small RNA (such as microRNA (miRNA), small interfering RNA (siRNA), and Piwi-interacting RNA (piRNA)), and long intergenic non-coding (linc) RNA. mRNA is a RNA encoding a protein, most of which has a length of 1,000 nt or more. miRNA, siRNA, piRNA and lincRNA are non-coding (nc) RNAs which do not encode proteins. Among ncRNAs, miRNA is a small RNA of about 19 to 30 nt in length. lincRNA, which is a long non-coding RNA having poly-A like mRNA, has a length of 200 nt or more (Non Patent Literature 1). The nucleic acid prepared in the method of the present invention is more preferably RNA having a length of 200 nt or more. The nucleic acid prepared is still more preferably at least one nucleic acid selected from the group consisting of mRNAs and lincRNAs.

In one embodiment, the method of the present invention may further comprise collecting SSLs of a subject. Examples of the skin from which SSLs are collected include, but not particularly limited to, the skin of any region of the body such as the head, face, neck, trunk and limbs; the skin having a disease such as atopy, acne, inflammation and a tumor; and the skin having a wound. Also, the skin from which SSLs are collected preferably does not comprise the skin of the palm, back, sole or finger.

Any means used to collect or remove SSLs from the skin can be used to collect SSLs from the skin of a subject. An SSL absorbent material, an SSL adhesive material, or a tool for scraping SSLs from the skin, as described below, can be preferably used. The SSL absorbent material or SSL adhesive material is not particularly limited so long as it is a material having an affinity for SSLs, and examples thereof include polypropylene and pulp. More specific examples of the procedure for collecting SSLs from the skin include a procedure for allowing SSLs to be absorbed into a sheet-like material such as an oil-blotting paper and an oil-blotting film; a procedure for bonding SSLs to a glass plate, a tape or the like; and a procedure for collecting SSLs by scraping SSLs with a spatula, a scraper or the like. The SSL absorbent material pre-impregnated with a highly lipid-soluble solvent may be used to improve the adsorption of SSLs. On the other hand, it is not preferred that the SSL absorbent material contains a highly water-soluble solvent or water, because the adsorption of SSLs is inhibited. The SSL absorbent material is preferably used in a dry state.

Isolation of a nucleic acid from the SSLs collected can be performed by using any method usually used for extracting or purifying a nucleic acid from a biological sample, for example, the phenol/chloroform method, the acid guanidinium thiocyanate-phenol-chloroform extraction (AGPC) method, a method using a column such as TRIzol (registered trademark) and RNeasy (registered trademark), a method using a special magnetic particle coated with silica, a method using a Solid Phase Reversible Immobilization magnetic particle, and extraction with a commercially available DNA or RNA extraction reagent such as ISOGEN.

(Method for Analyzing Nucleic Acid)

The nucleic acid derived from a skin cell of a subject and prepared by the method of the present invention can be used for various analyses or diagnoses using nucleic acids. Accordingly, the present invention also provides a method for analyzing a nucleic acid, comprising analyzing the nucleic acid prepared by the above-described method for preparing a nucleic acid according to the present invention. Examples of the analysis and diagnosis which can be performed by using the nucleic acid in SSLs prepared according to the present invention include:

(i) an analysis of gene expression and analysis of other genetic information on the skin of a subject, functional analysis on the skin of a subject based on the analyses, and the like;

(ii) an analysis of skin conditions of a subject, such as an evaluation or future prediction of physical conditions of the skin, a diagnosis and prognosis of skin diseases, an efficacy evaluation of skin external preparations, a diagnosis and prognosis of skin cancer and an evaluation of a minute change of the skin; and (iii) an analysis of conditions of regions other than the skin or the general condition of a subject, such as an evaluation or future prediction of general physical conditions of a subject, and a diagnosis or prognosis of various diseases such as a neurological disease, a cardiovascular disease, a metabolic disease and cancers.

More specific examples of the analysis and diagnosis using nucleic acids in SSLs are shown below.

Gene Expression Analysis

As shown in Examples described below, SSLs were rich in high molecular weight RNAs such as mRNA derived from a subject, whereas conventionally used biological samples such as urine, serum, saliva and horny layer comprised little high molecular weight RNA (Examples 1 to 3). SSLs are sources of mRNA which can be collected from a subject noninvasively, and useful as a biological sample for gene expression analysis. In addition, SSLs are suitable as a biological sample for gene expression analysis of the skin, particularly the sebaceous gland, hair follicle and dermis, because mRNA in SSLs reflects gene expression profiles of the sebaceous gland, hair follicle and dermis (Example 4).

Pathologic Diagnosis

According to a recent report, about 63% of RNAs the expressions of which change in cancer cells are mRNAs encoding proteins (Cancer Res. 2016, 76, 216-226). Therefore, it is considered that by measuring the expression status of mRNA, a change in physiological conditions of a cell due to a disease such as cancer can be grasped more faithfully and body conditions can be diagnosed more accurately. SSLs are rich in mRNAs, and also comprise mRNA for superoxide dismutase 2 (SOD2) which is reported to be associated with cancers (Physiol Genomics, 2003, 16, 29-37; Cancer Res, 2001, 61, 6082-6088). Therefore, SSLs are useful as a biological sample for diagnosis or prognosis of cancers such as skin cancer.

In recent years, it has been reported that the expressions of molecules in the skin vary in patients with a disease in tissues other than the skin such as obesity, Alzheimer's disease, breast cancer and cardiac disease, and thus it can be said that "the skin is a window to the body's health" (Eur J Pharm Sci. 2013, 50, 546-556). Therefore, by measuring the expression status of mRNAs in SSLs, there is a possibility that physiological conditions of regions of a subject other than the skin or general physiological conditions of a subject can be analyzed.

Non-Coding RNA Analysis

In recent years, the involvement of non-coding (nc)RNAs such as miRNA and lincRNA in cellular gene expression has attracted attention and has been studied actively. In addition, methods for diagnosing cancers and the like noninvasively or minimally invasively using urine or serum miRNA have been conventionally developed (for example, Proc Natl Acad Sci USA, 2008, 105, 10513-10518; Urol Oncol, 2010, 28, 655-661). ncRNAs such as miRNA and lincRNA prepared from SSLs can be used as samples for the above studies and diagnoses.

Screening or Detection of Nucleic Acid Markers

A nucleic acid marker for a disease or condition can be screened or detected by using a nucleic acid prepared from SSLs as a sample. The nucleic acid marker for a disease or condition used herein refers to a nucleic acid the expression of which is an indicator for determining a given disease or condition or a risk thereof. Preferably the nucleic acid marker is an RNA marker, and the RNA is preferably mRNA, miRNA or lincRNA. Examples of the disease or condition targeted by the nucleic acid marker include, but not limited to, various skin diseases, physical conditions of the skin (such as photoaging, drying, moisture or oil content, skin tension and dullness); and cancers such as skin cancer, and diseases in the tissues other than the skin such as obesity, Alzheimer's disease, breast cancer and cardiac disease, as described in the above section "Pathologic diagnosis." Analysis of nucleic acid expression can be performed according to known means such as RNA expression analysis using a real-time PCR, a microarray and a next-generation sequencer.

An example is a method for selecting a nucleic acid marker for a disease or condition. In this method, using a population having a predetermined disease or condition or risk thereof as subjects, nucleic acids derived from skin cells of the subject population are prepared according to the method for preparing a nucleic acid of the present invention. Expressions (such as expression levels) of the nucleic acids prepared from the population are compared with those of a control. Examples of the control include a population not having the predetermined disease or condition or risk thereof, and statistical data based thereon. The nucleic acid exhibiting expression different from that of the control can be selected as a marker or a candidate thereof for the predetermined disease or condition.

Another example is a method for detecting a nucleic acid marker for a disease or condition, or a method for determining a disease or condition or the risk thereof based on the detection of the marker. In this method, a nucleic acid derived from a skin cell of a subject is prepared from the subject in need of or desiring determination of a predetermined disease or condition or risk thereof according to the method for preparing a nucleic acid of the present invention. Then, the nucleic acid marker for the predetermined disease or condition is detected from the prepared nucleic acid. The disease or condition or the risk thereof of the subject is determined based on the presence or absence and the expression level of the nucleic acid marker.

(Kit for Preparing Nucleic Acid)

In a further aspect, the present invention provides a kit for preparing a nucleic acid derived from a skin cell of a subject, comprising a collecting tool for SSLs from the subject. Examples of the collecting tool for SSLs include an SSL absorbent material or an SSL adhesive material and a tool for scraping SSLs from the skin. The SSL absorbent material is preferably a flexible sheet-like material produced from such a material as polypropylene. Preferable examples of the SSL absorbent material include an oil-blotting paper and an oil-blotting film. The SSL absorbent material is preferably a material in a dry state which is free of a water-soluble solvent or water. The SSL adhesive material is preferably sheet-like or plate-like, and may be coated as necessary with an adhesive such as poly-L-lysine for adhering SSLs to the surface thereof. Preferable examples of the SSL adhesive material include a glass plate and a tape. Preferable examples of the tool for scraping SSLs include a spatula and a scraper.

The kit for preparing a nucleic acid according to the present invention may further comprise a reagent for isolating a nucleic acid from the SSLs collected with the above-mentioned collecting tool. A reagent usually used for extracting or purifying DNA or RNA from a biological sample can be used as the above reagent.

As an exemplary embodiment of the present invention, the following materials, manufacturing methods, applications and methods, and the like will be further disclosed herein. However, the invention will not be limited to these embodiments.

[1] A method for preparing a nucleic acid derived from a skin cell of a subject, comprising isolating the nucleic acid from skin surface lipids collected from the subject.

[2] The method according to [1], preferably further comprising collecting the skin surface lipids of the subject.

[3] The method according to [1] or [2], wherein the nucleic acid is preferably a nucleic acid derived from at least one region selected from the group consisting of the epidermis, sebaceous gland, hair follicle, sweat gland and dermis, and more preferably a nucleic acid derived from at least one region selected from the group consisting of the epidermis, sebaceous gland, hair follicle and sweat gland.

[4] The method according to any one of [1] to [3], wherein the nucleic acid is preferably RNA.

[5] The method according to [4], wherein the RNA has preferably a length of 200 nt or more.

[6] The method according to [4] or [5], wherein the RNA is preferably at least one selected from the group consisting of mRNA and lincRNA.

[7] The method according to any one of [1] to [6], wherein the skin surface lipids are preferably collected by using a skin surface lipid-absorbent material, a skin surface lipid-adhesive material, or a tool for scraping skin surface lipids from the skin.

[8] The method according to any one of [1] to [7], wherein the skin surface lipids are preferably skin surface lipids present on the skin of the head, face, neck, trunk or limbs; the skin having a disease; or the skin having a wound.

[9] The method according to any one of [1] to [8], wherein the skin surface lipids preferably do not comprise skin surface lipids on the skin of the palm, back, sole or finger.

[10] A method for analyzing a nucleic acid, comprising analyzing the nucleic acid prepared by the method according to any one of [1] to [9].

[11] A method for selecting a nucleic acid marker for a predetermined disease or condition, comprising:
  preparing nucleic acids by the method according to any one of [1] to [9] using a population having the predetermined disease or condition or risk thereof as a subject population; and
  comparing expressions of the prepared nucleic acids with those of a control.

[12] A method for detecting a nucleic acid marker for a predetermined disease or condition, comprising:
  preparing a nucleic acid of a subject by the method according to any one of [1] to [9]; and
  detecting the nucleic acid marker for the predetermined disease or condition from the prepared nucleic acid.

[13] A kit for preparing a nucleic acid derived from a skin cell of a subject, comprising a collecting tool for skin surface lipids from the subject.

[14] The kit according to [13], wherein the collecting tool is preferably a skin surface lipid-absorbent material, a skin surface lipid-adhesive material, or a tool for scraping skin surface lipids from the skin.

[15] The kit according to [13] or [14], preferably further comprising a reagent for isolating the nucleic acid from the collected skin surface lipids.

[16] The kit according to any one of [13] to [15], wherein the nucleic acid is preferably a nucleic acid derived from at least one region selected from the group consisting of the epidermis, sebaceous gland, hair follicle, sweat gland and dermis, and more preferably a nucleic acid derived from at least one region selected from the group consisting of the epidermis, sebaceous gland, hair follicle and sweat gland.

[17] The kit according to any one of [13] to [16], wherein the nucleic acid is preferably RNA.

EXAMPLES

Hereinafter, the present invention will be further specifically described with reference to the following Examples, but is not intended to be limited thereto.

Example 1

Analyses of RNAs in Various Biological Samples

RNA in each of the horny layer of the skin, skin surface lipids (SSLs), serum, urine, and saliva was analyzed:

Four layers of the horny layer of the forehead of a subject were collected in series in the depth direction from the same region with an acrylic tape (2.5 cm×3.0 cm) according to the method described in Non Patent Literature 2, and RNA was then extracted therefrom.

SSLs were collected from the entire face of the subject with an oil-blotting film (3M Japan Limited). Next, the oil-blotting film was cut to an appropriate size, and RNA was extracted with TRIzol (registered trademark) reagent (Life Technologies Japan Ltd.) according to the protocol attached thereto.

Human serum, urine and saliva were purchased from Cosmo Bio Co., Ltd. Saliva was centrifuged at 15,000 rpm for 5 minutes to remove mucin and oral cells contaminating it, and the supernatant was then transferred to a new tube and used as a sample. RNA was extracted from a sample of each of the serum, urine and saliva with TRIzol (registered trademark) LS reagent (Life Technologies Japan Ltd.) according to the protocol attached thereto.

Next, each of the extracted RNAs was analyzed with Agilent RNA6000 Pico Kit (Agilent Technologies Japan, Ltd.).

The results are shown in FIG. 1. RNA in SSLs comprised 23S and 16S rRNA derived from bacteria as well as 28S rRNA derived from human and 18S rRNA considered to be derived from fungi and human. No peak was observed in the horny layer, and therefore, it was presumed to contain little RNA. A peak of a low molecular weight RNA (small RNA) was observed in RNA extracted from each of serum, urine and saliva, which corresponds with a conventional report (Non Patent Literature 1) that a low molecular weight RNA such as miRNA exists in each of serum, urine and saliva.

Example 2

Proportion of the RNAs Derived from Each Species Present in SSLs

In order to calculate the proportion of RNAs derived from each species present in SSLs, the copy number of each of the sequence of rRNA present commonly in bacteria in SSLs, the sequence of rRNA present commonly in fungi in SSLs, and the sequence of human rRNA in SSLs was determined by an absolute quantitative assay based on real-time PCR.

For bacterial 16S rRNA, the 16S rRNA region of *Staphylococcus epidermidis* strain JCM2414 was cloned into pUC118. For fungal 26S rRNA, 265 rRNA region of *Malassezia globosa* strain CBS7874 was cloned in pUC118. For human 18S rRNA, human 18S rRNA region was cloned in pcDNA3.1. Each of these plasmid DNAs was used as a standard sample for real-time PCR. A PCR primer was designed for bacteria based on the information of the consensus sequence of 16S rRNA (Appl Environ Microbiol, 2012, 78, 5938-5941), for fungi based on the information of the consensus sequence of 26S rRNA (PLoS One, 2012, e 32847), and for human based on the information of the 18S rRNA (Table 1).

TABLE 1

| Primer name | Sequence (5'-3') | SEQ ID: No. | Probe type | Target |
|---|---|---|---|---|
| 27F | AGAGTTTGATCMTGGCTCAG | 1 | SYBR | All bacteria |
| 519R | GWATTACCGCGGCKGCTG | 2 | Green | (16S rRNA) |

TABLE 1-continued

| Primer name | Sequence (5'-3') | SEQ ID: No. | Probe type | Target |
|---|---|---|---|---|
| NL-1 | GCATATCAATAAGCGGAGGAAAG | 3 | SYBR Green | All fungi (26S rRNA) |
| NL-4 | GGTCCGTGTTTCAAGACGG | 4 | | |
| TaqMan probe (Hs99999901_s1) | Unknown | | FAM | Human (18S rRNA) |

RNA in SSLs collected from each of three subjects was reverse transcribed using SuperScript III First-Strand Synthesis System for RT-PCR (Life Technologies Japan, Ltd.), and the copy number of rRNA of each species in SSLs was calculated by real-time PCR using the resulting cDNA as a template. The calculation results show, similar to the results in Example 1, that RNAs in SSLs comprise rRNAs derived from bacteria, fungi and human, among which rRNA derived from human accounts for a major proportion (Table 2).

TABLE 2

| | Copy number | | |
|---|---|---|---|
| Subjects | Bacteria (16S rRNA) | Fungi (26S rRNA) | Human (18S rRNA) |
| No. 1 | 2.9E+05 | n.d. | 1.2E+06 |
| No. 2 | 2.7E+06 | 5.6E+04 | 3.7E+07 |
| No. 3 | 2.0E+06 | 1.4E+04 | 9.4E+06 | n.d.: not detected

Example 3

Detection of mRNAs in Various Biological Samples

The presence or absence of mRNA in each of various biological samples used in Example 1 was evaluated with the ubiquitously expressed mRNAs of GAPDH and SOD2 as indices.

Each of RNAs in various biological samples extracted in Example 1 was reverse transcribed using Superscript III First-Strand Synthesis System for RT-PCR (Life Technologies Japan, Ltd.), and RT-PCR was performed using the resulting cDNA as a template. RNA isolated from human epidermal cells was used as a positive control. The RT-PCR was performed using Advantage 2 PCR Kit (Takara Bio Inc.) and the primers shown in Table 3 to amplify cDNAs of GAPDH and SOD2 according to a PCR program (95° C., 5 minutes→[95° C., 15 seconds→60° C., 30 seconds→72° C., 30 seconds]×35 cycles→72° C., 7 minutes). After the PCR, electrophoresis was performed using 2% agarose gel and TrackIt 1 Kb Plus DNA Ladder (Lite Technologies Japan, Ltd.) to detect the target bands.

TABLE 3

| Primer name | Sequence (5'-3') | SEQ ID: No. | Product size (bp) |
|---|---|---|---|
| GAPDH-F | CCCTTCATTGACCTCAACTAC | 5 | 349 |
| GAPDH-R | AGTGAGCTTCCCGTTCAGCT | 6 | |

TABLE 3-continued

| Primer name | Sequence (5'-3') | SEQ ID: No. | Product size (bp) |
|---|---|---|---|
| SOD2-F | CCCTTCATTGACCTCAACTAC | 7 | 257 |
| SOD2-R | AGTGAGCTTCCCGTTCAGCT | 8 | |

Figure 2:
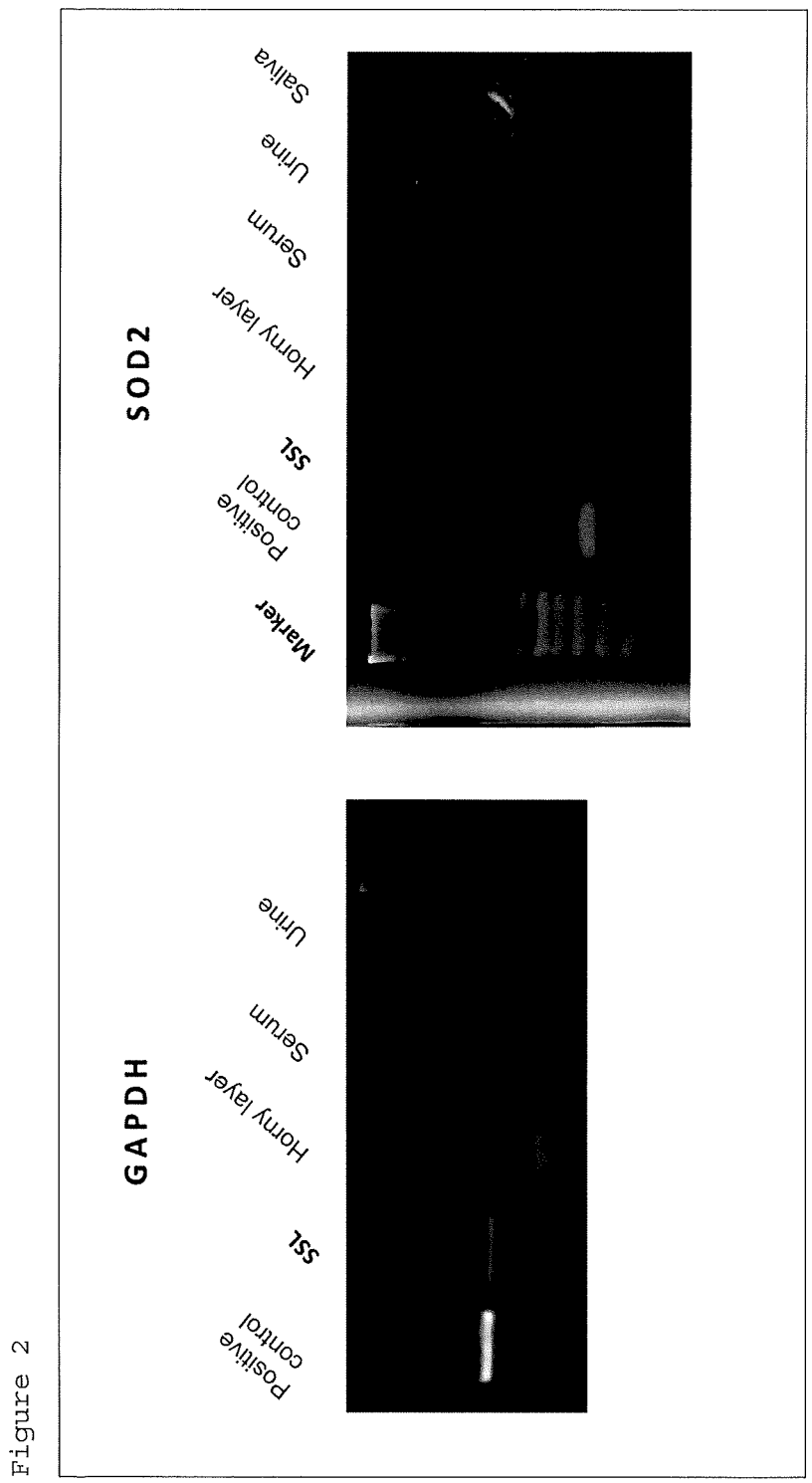
FIG. 2 mRNA expressions for RNAs derived from various biological samples.

The results are shown in FIG. 2. Bands for both GAPDH and SOD2 were detected in SSLs at the same position as the positive control, confirming the presence of mRNA. Therefore, it was shown that SSLs comprise mRNAs and they can be used as biological samples for analysis of gene expression of the skin. On the other hand, for the horny layer, serum, urine and saliva, neither band for GAPDH nor for SOD2 was able to be confirmed.

SOD2, mRNA for which was detected in SSLs, is an enzyme converting a super oxide anion, which is harmful to cells, into hydrogen peroxide, and its reverence to cancer has been reported. It has reported that heterozygous mice deleted in this gene have a large accumulation of DNA damage in the whole-body tissues; have a higher mortality rate than that of the wild type thereof when oxidative stress is induced; and have a higher incidence of cancer than that of the wild type thereof (Physiol Genomics, 2003, 16, 29-37). On the other hand, it has reported that mice having SOD2 overexpressed in the skin have a lower incidence of skin cancer than that of the wild type thereof even when oxidative stress is continuously applied to the skin (Cancer Res, 2001, 61, 6082-6088). Therefore, SSLs comprising SOD2 mRNA are also expected as a biological sample for diagnosis of the onset risk of or prognosis of cancers such as skin cancer.

Example 4

Comprehensive Analysis of Gene Expression of RNA in SSLs Using Next-Generation Sequencer (1) The feasibility of comprehensive analysis of gene expression using SSLs as a sample was confirmed. SSLs were collected from the face of each of three subjects using an oil-blotting film and were divided into two equal parts to confirm technical errors, and RNA was then extracted from each part. A comprehensive analysis of gene expression was performed using the extracted RNA by a next-generation sequencer Ion Proton system (Life Technologies Japan Ltd.). Specifically, a library was constructed from the collected RNA using Ion AmpliSeqTranscriptome Human Gene Expression Kit (Life Technologies Japan Ltd.) according to the protocol attached thereto, and subjected to emulsion PCR by the Ion chef system (Life Technologies Japan Ltd.). The resulting PCR product was loaded on Ion PI Chip and sequenced using Ion Proton system to calculate the number of reads mapped on each of the marker gene of the epidermis, sweat gland, dermis, hair follicle and sebaceous gland. Marker genes were selected based on literature information (Int J Mol Med, 2014, 34, 997-1003; J Invest Dermatol, 1997, 108, 324-329; J Invest Dermatol, 2002, 119, 1137-1149; Development; 2013, 140, 4870-4880).

Results are shown in FIG. 3. The marker genes of the epidermis, sweat gland, hair follicle and sebaceous gland were detected from SSLs. The marker gene of the dermis was also detected slightly. This shows that SSLs mainly comprise RNA molecules derived from the epidermis, sweat gland, hair follicle and sebaceous gland, and also comprise RNA molecules derived from the dermis slightly.

Figure 4:
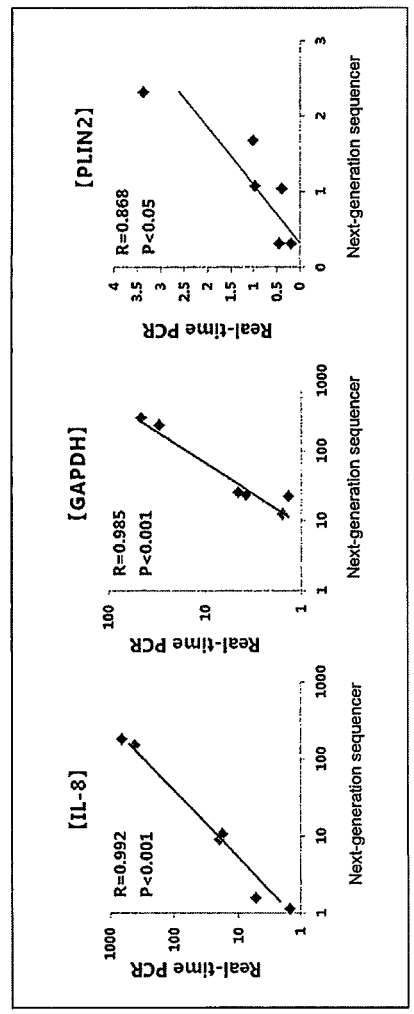
FIG. 4 Correlation of analysis results of expression levels between a next-generation sequencer and a real-time PCR.

(2) The reliability of the analysis results by the next-generation sequencer obtained in the above (1) was confirmed by real-time PCR which has the highest reliability as a method for quantitating mRNA. cDNA was synthesized from each of the RNA samples prepared in (1) using SuperScript III First-Strand Synthesis System for RT-PCR, and gene expressions of IL-8, GAPDH and PLIN2 as representative genes detected by the next-generation sequencer were quantified by real-time PCR and compared with the analysis results obtained by the sequencer in (1). The analysis results by the next-generation sequencer and the analysis results by the real-time PCR analysis significantly correlated positively with each other for any of gene expressions of IL-8, GAPDH and PLIN2, which confirmed the reliability of the analysis results obtained by the next-generation sequencer (FIG. 4).

Example 5

Analysis of RNA in Skin Surface Lipids

The human skin sample collected with the moistened swab reported in the above-mentioned Non Patent Literature 3 was compared with the skin surface lipids according to the present patent application.
(Sample Collection)

A range of 3 cm×5 cm on each of the left and right sides from the middle of the forehead was selected as a range for sample collection. Skin surface substances were collected from one side with an oil-blotting film (polypropylene, 3 cm×5 cm, 3M Japan Limited) and from the other side with a culture swab (Culture SWAB EZ, polyurethane, Nippon Becton Dickinson Company, Ltd.) impregnated with and moistened with PBS by repeating three times the procedure of rubbing the entire surface within the collection range while applying a constant force thereto.
(Evaluation of Content of Lipids)

The content of lipids in each of the collected samples was evaluated using as an indicator the amount of triglyceride, which is a major component of skin surface lipids. The oil-blotting film used for the sample collection was cut to an appropriate size and the tip portion of the culture swab used for the sample collection was collected, and lipids were extracted therefrom using Bligh-Dyer method. Specifically, chloroform, methanol, and phosphate buffered saline (PBS) were added to the sample, and the mixture was then thoroughly shaken to extract lipids. Chloroform and PBS were further added to the extract, and the mixture was shaken thoroughly, and then separated into an organic phase and an aqueous phase by a centrifuge to recover the organic phase. The organic phase was dried by blowing nitrogen gas thereto at a temperature of 30° C. and then dissolved in 1 mL of a solution of 1% Triton X-100 (Sigma Aldrich) in PBS to prepare a sample solution. Each of an oil-blotting film and a culture swab not used for the sample collection was also treated as in the same manner to prepare a blank sample solution. Absorbance at 570 nm was measured using Serum Triglyceride Quantification Kit (CELL BIOLABS, INC.) according to the protocol attached thereto to quantify the amount of triglyceride in each sample solution.

The quantification results of the amounts of triglycerides are shown in Table 4. When skin surface lipids were collected with the oil-blotting film, the concentration of triglyceride in the sample solution was 100 μM or more. On the other hand, when skin surface substances were collected with the moistened cotton swab, the concentration of triglyceride in the sample solution was not more than the detection limit of 10 μM, which was not different from that in the blank. Therefore, it is shown that the skin surface substances collected with the moistened cotton swab comprise substantially no component derived from the skin surface lipids.

TABLE 4

| Sample | Absorbance (570 nm) | Concentration of triglyceride (μM) |
| --- | --- | --- |
| Oil-blotting film (blank) | 0.047 | <10 |
| Oil-blotting film (sample) | 0.1655 | 117.8 |
| Culture swab (blank) | 0.055 | <10 |
| Culture swab (sample) | 0.055 | <10 |

(Analysis of Human RNA Molecule)

The skin surface substances were collected from each of the left and right sides from the middle of the forehead with an oil-blotting film and a culture swab moistened with PBS, as described above. The oil-blotting film was cut to an appropriate size, and the tip portion of the culture swab was collected, and RNA was extracted therefrom using RNeasy Lipid Tissue Mini Kit (QIAGEN) according to the protocol attached thereto. The extracted RNA was precipitated with ethanol, dissolved in 10 μL of water, and subjected to a comprehensive analysis of gene expression by a next-generation sequencer Ion S5/XL system (Life Technologies Japan Ltd.). Specifically, a library was constructed from the collected RNA using Ion AmpliSeq Transcriptome Human Gene Expression Kit (Life Technologies Japan Ltd.) according to the protocol attached thereto, and subjected to emulsion PCR by the Ion chef system (Life Technologies Japan Ltd.). The resulting PCR product was loaded on Ion 540 Chip and sequenced using the Ion S5/XL system.

The results of comprehensive expression analysis of RNA in the skin surface substances collected with each of the oil-blotting film and the culture swab showed that among human genes from which sequence fragments of 10 reads or more could be detected for one gene, genes observed only in the oil-blotting film collection were 5,294 genes whereas genes observed only in the culture swab collection were 132 genes, and genes observed commonly in the oil-blotting film collection and the culture swab collection were 625 genes. These results show that the skin surface lipids collected with the oil-blotting film comprise a wider variety of RNA molecules as compared with the skin surface substances collected with the moistened culture swab and comprising substantially no skin surface lipid and that the skin surface lipids are very useful in performing gene analyses and condition diagnoses of subjects.

The invention claimed is:

1. A method for preparing a nucleic acid derived from a human subject, comprising collecting a skin surface lipids sample comprising secretions secreted from a sebaceous gland of the human subject on a skin surface of the human subject and isolating the nucleic acid from the collected skin surface lipids sample, wherein the nucleic acid is human RNA and wherein said collecting comprises applying to the skin surface of the human subject a surface skin lipid absorbent material which is an oil-blotting film made of polypropylene, wherein the surface skin lipid absorbent material is not a surface skin lipid adhesive material.

2. The method according to claim 1, wherein the skin surface lipids sample does not comprise skin surface lipids on the skin of the palm, back, sole or finger.

3. The method according to claim 1, wherein the human RNA comprises one or more RNAs having a length of 200 nt or more.

4. The method according to claim 1, wherein the human RNA is at least one selected from the group consisting of mRNA and lincRNA.

5. The method of claim 1, further comprising determining a gene expression level of one or more genes of the human subject based on the isolated human RNA.

6. The method of claim 1, further comprising impregnating the surface skin lipid absorbent material with a highly lipid-soluble solvent prior to said applying.

7. The method of claim 1, wherein the surface skin lipid absorbent material is free of a water-soluble solvent or water.

8. The method of claim 1, wherein the skin surface of the human subject is a skin surface on a face or a head of the human subject.

9. The method of claim 1, wherein the surface skin lipid absorbent material is used in a dry state.

* * * * *